Figure 1:
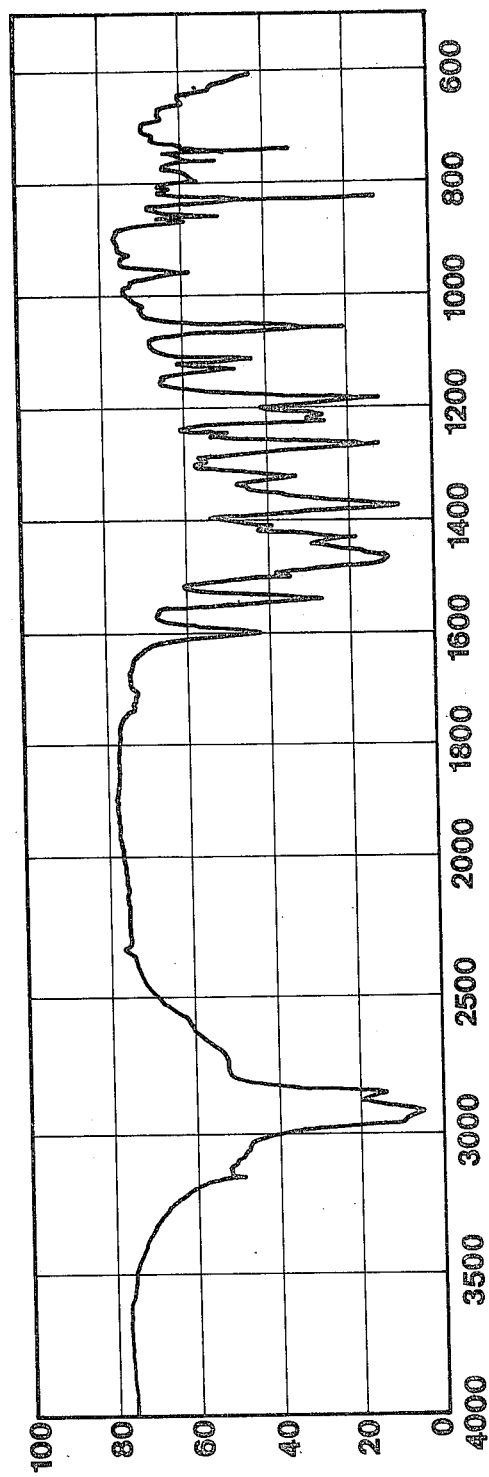

United States Patent [19]

Scalesciani

[11] Patent Number: 4,476,138
[45] Date of Patent: Oct. 9, 1984

[54] 1-METHYL-5-NITRO-(2-SUBSTITUTED)-2H-IMIDAZOLE DERIVATIVES, AND USE AS BACTERICIDAL AND PROTOZOACIDAL AGENTS

[75] Inventor: Juan B. A. Scalesciani, Buenos Aires, Argentina

[73] Assignee: Farmatis S.r.l., Milan, Italy

[21] Appl. No.: 513,915

[22] Filed: Jul. 14, 1983

[30] Foreign Application Priority Data

Aug. 20, 1982 [IT] Italy ................................ 22911 A/82

[51] Int. Cl.$^3$ ................... A61K 31/415; C07D 233/22
[52] U.S. Cl. ............................... 424/273 R; 548/338; 548/339
[58] Field of Search .............................. 548/338, 339; 424/273 R

[56] References Cited

U.S. PATENT DOCUMENTS 3,686,203 8/1972 Somerset et al. ................... 548/339

FOREIGN PATENT DOCUMENTS 892911 8/1982 Belgium .
2436780 11/1978 France ............................... 548/338
8206811 4/1982 France .

OTHER PUBLICATIONS

Goodman and Gilman, The Pharmacological Basis of Therapeutics, Sixth Ed., p. 28, Col. 2, 1st Paragraph.
Casiragi et al., J.C.S. Perkin I, (Eng.), 1974, pp. 2077–2079.

Primary Examiner—Alan L. Rotman
Assistant Examiner—J. G. Mullins
Attorney, Agent, or Firm—Stevens, Davis, Miller & Mosher

[57] ABSTRACT

A description is given of new compounds of structural formula:

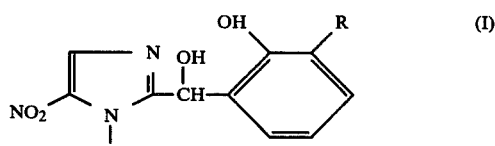

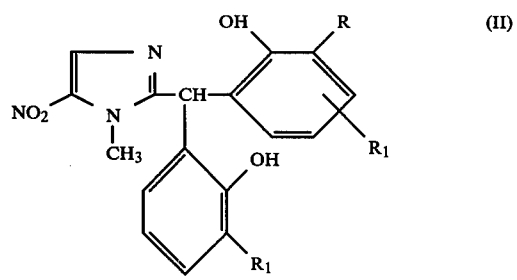

in which R is alkyl and $R_1$ is H or alkyl; and a process for preparing these compounds starting from 1-methyl-5-nitro-imidazolyl-2-carboxyaldehyde and o-alkyl-phenols.

The new compounds are used as drugs for illnesses deriving from protozoa and anaerobic bacteria.

5 Claims, 2 Drawing Figures

1-METHYL-5-NITRO-(2-SUBSTITUTED)-2H-IMIDAZOLE DERIVATIVES, AND USE AS BACTERICIDAL AND PROTOZOACIDAL AGENTS

This invention relates to a new class of 1-methyl-5-nitro-imidazoline derivatives included in the general formula:

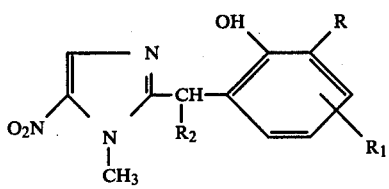

in which R is a linear or branched alkyl of 1-6 carbon atoms, $R_1$ is H or linear or branched alkyl of 1-6 carbon atoms, and $R_2$ is —OH or

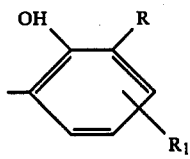

Compounds of the above general formula show antibacterial or antiprotozoan activity. In particular, these compounds are active against anaerobic micro-organisms and Trichomonas vaginalis. Thus, these compounds find use as principal active ingredients in therapeutic compositions for treating illnesses of a bacterial and protozoan nature such as trichomoniasis, amebiasis, giardiasis and infections deriving from gram-positive and gram-negative anaerobic bacteria in their various forms.

In contrast to known nitroimidazoline compounds used up to the present time in therapy, the compounds of the present invention do not possess mutagenic power and have very low toxicity. Compounds of formula (I) in which R is tert-butyl and $R_1$ is H have proved particularly valuable for therapeutic use.

In preparing compounds of class (I), the starting substances used are an ortho-alkyl substituted phenol, possibly containing other alkyl substituents on the benzene nucleus, and 1-methyl-5-nitro-imidazolyl-2-carboxyaldehyde:

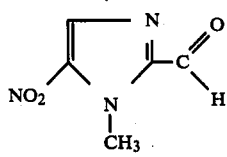

The reaction on which the process according to the present invention is based has been generally described for aromatic aldehydes and phenols by Casiraghi et al. in J. C. S. Perkin I (1974) pages 2077–2079.

The process for preparing the compounds of formula (I) comprises a first stage in which the phenol $RC_6H_4OH$ is reacted in an anhydrous polar solvent with an alkyl magnesium halide $R'MgX$ (Grignard compounds) to thus obtain the phenoxy-magnesium halide $RC_6H_4OMgX$. This latter compound is reacted in an anhydrous solvent with 1-methyl-5-nitro-imidazolyl-2-carboxyaldehyde in a molecular ratio of either 1:1 or 2:1, depending upon whether a compound is required in which $R_2$ is hydroxyl or a phenol radical, respectively.

The final product is obtained by treating the magnesium halide intermediate containing the —OMgX group with hydrochloric acid.

The anhydrous polar solvent used in the first stage of the reaction is preferably a dialkyl ether, such as diethyl ether, or a cyclic ether such as tetrahydrofuran. Benzene is preferably used in the next stage.

As initially stated, the new products possess antiprotozoan and antibacterial activity.

In particular, it has been found that the products corresponding to the two meanings of $R_2$, in which R is tert-butyl, are active in vitro against Trichomonas vaginalis deriving from hospital isolation in doses of 0.5 mcg/ml.

The same compounds have shown a Minimum Inhibiting Concentration equal to or less than 12.5 µg/ml against a certain number of gram-positive and gram-negative bacteria such as Streptococcus pyogenes, Diplococcus pneumoniae, Klebsiella pneumoniae, Salmonella pullorum, Brucella bronchiseptica, Bacillus subtilis.

The $LD_{50}$ by oral administration in the mouse is 7000 mg/Kg±10%, and the $LD_{50}$ by oral administration in the rate is 7500 mg/Kg±10%.

The new products therefore possess an extremely favourable therapeutic index, in addition, as already stated, to the absence of any mutagenic power, as demonstrated by the Ames test (with and without metabolic activation).

In addition to use in human therapy, the new products can be used in the veterinary field against many illnesses of bacterial or protozoan origin.

The compounds of the present invention can be administered in any convenient manner, i.e. can be applied topically, administered orally or injected parenterally, by using therapeutically acceptable diluents, excipients and lubricants.

Daily administrations of between 100 and 1000 mg/d have given good results.

In order to make the new compounds according to the present invention more easily reproducible, two embodiments are described hereinafter by way of non-limiting example.

EXAMPLE 1

Preparation of the compound:

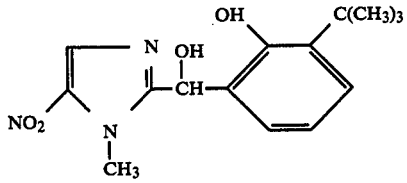

5-nitro-1-methyl-imidazolyl-2-hydroxy-3-tert.butyl-phenylcarbinol.

150 g (1 mole) of 2-tert.butyl-phenol are dissolved in 1000 ml of anhydrous ethyl ether, and 1 mole of ethyl-magnesium bromide dissolved in 1000 ml of anhydrous ethyl ether is fed slowly into this solution under agitation, while maintaining ambient temperature.

Most of the ether is removed from the solution obtained in this manner, after which 1000 ml of anhydrous benzene are added, and the solution is distilled to completely eliminate the ether. Finally, it is cooled and 1-methyl-5-nitro-imidazolyl-2-carboxyaldehyde (1 mole) dissolved in anhydrous benzene is then added.

The reaction is accelerated by raising the solution to boiling point.

Finally, 2N hydrochloric acid is added to the reaction solution until pH 7 is attained.

The magnesium converted in this manner into the halide passes into the aqueous phase, and is removed.

The final product is obtained from the benzene solution treated in this manner, by evaporation.

The product was identified by IR spectrum (see FIG. 1).

EXAMPLE 2

Preparation of the compound:

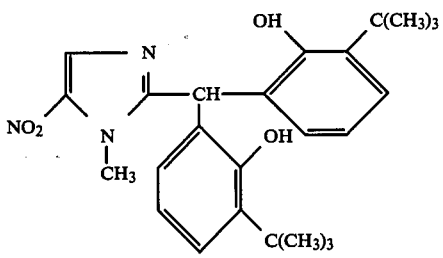

5-nitro-1-methyl-imidazolyl-bis(2-hydroxy-3-tert.butyl-phenyl)methane.

The procedure described in Example 1 is carried out, but using double the quantity of phenol (2 moles) and ethyl magnesium bromide. The final product is obtained after neutralization to pH 7 with 2N HCl.

Figure 2:
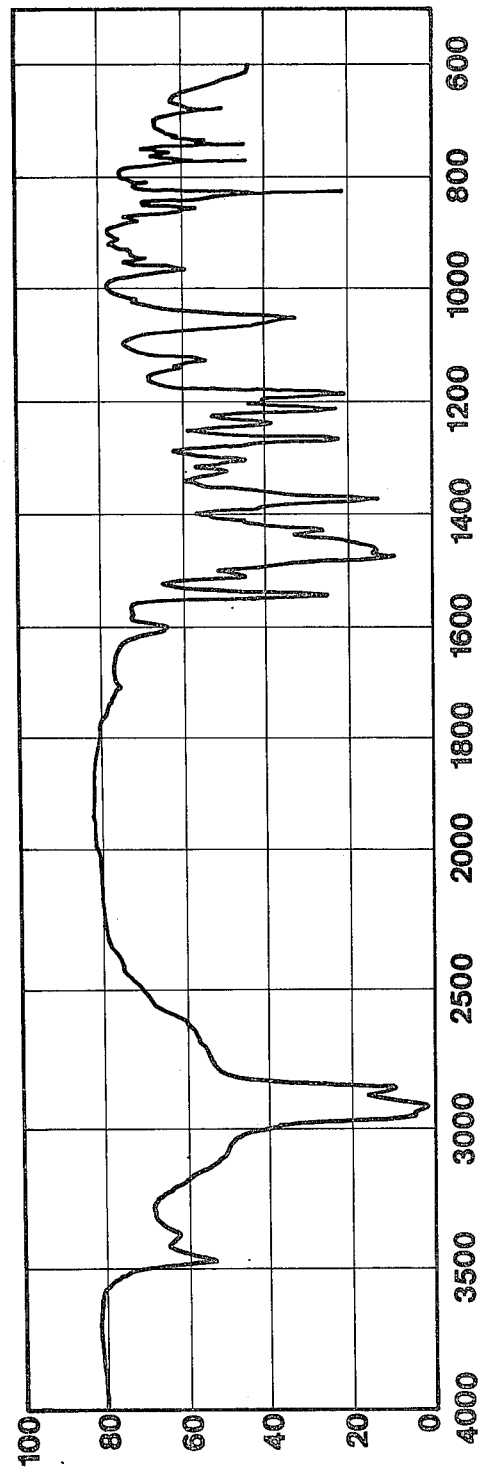

The product was identified by IR spectrum (see FIG. 2).

I claim:
1. Compounds of formula

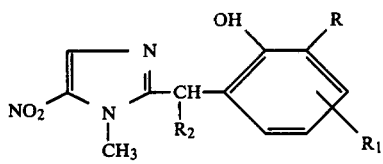

in which R is linear or branched alkyl of 1–6 carbon atoms, $R_1$ is H or linear or branched alkyl of 1–6 carbon atoms, and $R_2$ is OH or

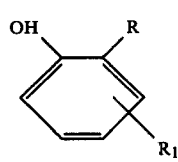

in which R and $R_1$ are as heretofore defined.

2. Compounds as claimed in claim 1, wherein R is a tert-butyl group.

3. A pharmaceutical bactericidal composition useful against pathogenic bacteria such as *Streptococcus pyogenes, Diplococcus pneumoniae, Klebsiella pneumoniae, Salmonella pullorum, Brucella bronchiseptica* and *Bacillus subtilis*, said composition comprising a bactericidal effective amount of a compound defined in claim 1 and a pharmaceutically acceptable carrier.

4. A pharmaceutical trichomonacidal composition useful against Trichomonas vaginalis, comprising a trichomonacidal effective amount of a compound defined in claim 1 and a pharmaceutically acceptable carrier.

5. The pharmaceutical trichomonacidal composition of claim 4, wherein R is tert-butyl.

* * * * *